(12) United States Patent
Tomoto

(10) Patent No.: US 8,509,509 B2
(45) Date of Patent: Aug. 13, 2013

(54) IMAGE PROCESSING APPARATUS AND IMAGE PROCESSING METHOD

(75) Inventor: Yusuke Tomoto, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/206,072

(22) Filed: Aug. 9, 2011

(65) Prior Publication Data

US 2012/0076373 A1    Mar. 29, 2012

Related U.S. Application Data

(63) Continuation of application No. PCT/JP2011/058316, filed on Mar. 31, 2011.

(30) Foreign Application Priority Data

Jun. 30, 2010    (JP) .................................. 2010-149971

(51) Int. Cl.
*G06K 9/00*      (2006.01)
*A61B 1/00*      (2006.01)
*A61B 1/04*      (2006.01)

(52) U.S. Cl.
USPC ........................... 382/128; 600/103; 600/118

(58) Field of Classification Search
USPC ........................... 382/128–132; 600/103, 118
See application file for complete search history.

(56) References Cited

U.S. PATENT DOCUMENTS

| 2007/0133894 A1 | 6/2007 | Kiraly et al. |
| 2009/0097730 A1 | 4/2009 | Kasai et al. |
| 2010/0092055 A1* | 4/2010 | Matsuda ...................... 382/128 |
| 2010/0124365 A1* | 5/2010 | Kanda ......................... 382/128 |

FOREIGN PATENT DOCUMENTS

| EP | 2 156 782 A1 | 2/2010 |
| JP | 10-091758 | 4/1998 |
| JP | 2006-346094 | 12/2006 |
| JP | 2008-307229 | 12/2008 |
| WO | WO 2008/152924 A1 | 12/2008 |

OTHER PUBLICATIONS

Frangi, et al "Multi-scale Vessel Enhancement Filtering" (LNCS, vol. 1496, Springer Verlag, Berlin, Germany 1998, pp. 130-137).*

(Continued)

*Primary Examiner* — Amara Abdi
(74) *Attorney, Agent, or Firm* — Scully, Scott, Murphy & Presser, P.C.

(57) ABSTRACT

An image processing apparatus of the invention includes a first feature value calculation unit adapted to calculate a first feature value for each pixel in an image picked up of living tissue, where the first feature value represents a value of an index which indicates what shape a local region; a second feature value calculation unit adapted to calculate a degree of concentration of a gradient vector as a second feature value based on the gradient vector for each pixel in the image; an evaluation value calculation unit adapted to calculate a geometric evaluation value for each pixel, based on calculation results of the first feature value and the second feature value; and a region extraction unit of separately extracting a candidate region of the linear structure and a candidate region of the massive structure based on a calculation result of the geometric evaluation value.

2 Claims, 6 Drawing Sheets

(56) References Cited

OTHER PUBLICATIONS

Berkman, S. et al., ("False-positive reduction using Hessian features in computer-aided detection of pulmonary nodules on thoracic CT images", Proceedings of SPIE, vol. 5747, Jan. 1, 2005, pp. 790-795).*

Berkman et al ("False-positive reduction using Hessian features in computer-aided detection of pulmonary nodules on thoracic CT images", Proceedings of SPIE, vol. 5747, Jan. 1, 2005, pp. 790-795).*

Frangi, Alejandro F., et al., "Multiscale Vessel Enhancement Filtering", LNCS, vol. 1496, Springer Verlag, Berlin, Germany, p. 130-137.

Berkman, S. et al., "False-positive reduction using Hessian features in computer-aided detection of pulmonary nodules on thoracic CT images", Proceedings of SPIE, vol. 5747, Jan. 1, 2005, pp. 790-795, XP55043672.

Berkman, S. et al, "Computerized lung nodule detection on screening CT scans: Performance on juxta-pleural and internal nodules", Proceedings of SPIE, Mar. 2, 2006, pp. 61445S-61445S-6, XP55043674.

Shikata, H. et al., "Quantitative evaluation of spatial distribution of line structure in the lung for computer-aided diagnosis of pulmonary nodules", Systems & Computers in Japan, Wiley, Hoboken, NJ, US, vol. 34, No. 9, Aug. 1, 2003, pp. 58-70, XP009164421.

Extended Supplementary European Search Report dated Nov. 16, 2012 from related application EP 11800482.9-2205.

* cited by examiner

IMAGE PROCESSING APPARATUS AND IMAGE PROCESSING METHOD

CROSS REFERENCE TO RELATED APPLICATION

This application is a continuation application of PCT/JP2011/058316 filed on Mar. 31, 2011 and claims benefit of Japanese Application No. 2010-149971 filed in Japan on Jun. 30, 2010, the entire contents of which are incorporated herein by this reference.

BACKGROUND OF THE INVENTION

1. Field of the Invention

The present invention relates to an image processing apparatus and image processing method, and more particularly, to an image processing apparatus and image processing method used for diagnosis and the like of living tissue.

2. Description of the Related Art

Recently, in order to help identify a lesion (abnormal area) in images picked up of living tissue in a body cavity using an endoscope and the like, studies have been conducted on image processing for detecting a running pattern of submucosal blood vessels and/or a predetermined structure and the like of epithelial tissue in the images.

For example, image processing disclosed by Alejandro F. Frangi, Wiro J. Niessen, Koen L. Vincken and Max A. Viergever: "Multiscale Vessel Enhancement Filtering", LNCS, vol. 1496, Springer Verlag, Berlin, Germany, pp. 130-137 involves modeling a linear structure by means of eigenvalues obtained through computations using a Hesse matrix, calculating a predetermined evaluation value using the eigenvalues, and enhancing a linear structure contained in an image according to a magnitude of the predetermined evaluation value.

SUMMARY OF THE INVENTION

An image processing apparatus according to one aspect of the present invention includes: a first feature value calculation unit adapted to calculate a first feature value for each pixel in an image picked up of living tissue, where the first feature value represents a value of an index which indicates what shape a local region including a pixel of interest and each pixel in a neighborhood of the pixel of interest has; a second feature value calculation unit adapted to calculate a degree of concentration of a gradient vector as a second feature value based on the gradient vector defined by a gradient direction and a gradient intensity calculated for each pixel in the image, where the degree of concentration of the gradient vector represents a state of distribution of the gradient direction in the local region; an evaluation value calculation unit adapted to calculate a geometric evaluation value for each pixel in the image, where a value which enables distinguishing between a linear structure and a massive structure contained in the image is calculated as the geometric evaluation value based on calculation results of the first feature value and the second feature value; and a region extraction unit adapted to separately extract a candidate region estimated to contain the linear structure and a candidate region estimated to contain the massive structure based on a calculation result of the geometric evaluation value.

An image processing method according to another aspect of the present invention includes: a first feature value calculation step of calculating a first feature value for each pixel in an image picked up of living tissue, where the first feature value represents a value of an index which indicates what shape a local region including a pixel of interest and each pixel in a neighborhood of the pixel of interest has; a second feature value calculation step of calculating a degree of concentration of a gradient vector as a second feature value based on the gradient vector defined by a gradient direction and a gradient intensity calculated for each pixel in the image, where the degree of concentration of the gradient vector represents a state of distribution of the gradient direction in the local region; an evaluation value calculation step of calculating a geometric evaluation value for each pixel in the image, where a value which enables distinguishing between a linear structure and a massive structure contained in the image is calculated as the geometric evaluation value based on calculation results of the first feature value and the second feature value; and a region extraction step of separately extracting a candidate region estimated to contain the linear structure and a candidate region estimated to contain the massive structure based on a calculation result of the geometric evaluation value.

DETAILED DESCRIPTION OF THE PREFERRED EMBODIMENT

An exemplary embodiment of the present invention will be described below with reference to the drawings.

FIGS. 1 to 7 concern the embodiment of the present invention.

Figure 1:
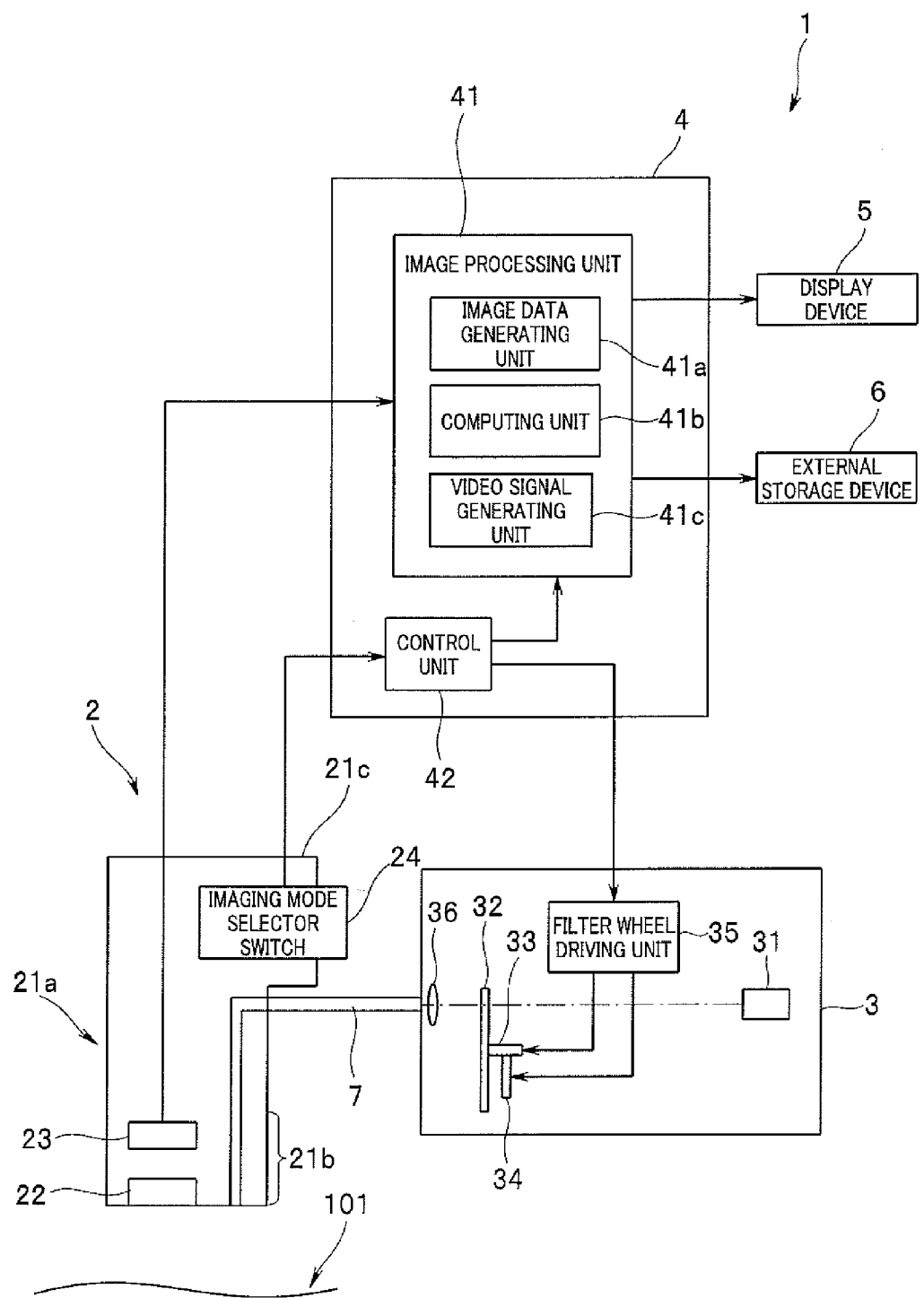
FIG. 1 is a diagram showing an exemplary configuration of principal part of an endoscope apparatus equipped with an image processing apparatus according to an embodiment of the present invention.

As shown in FIG. 1, an endoscope apparatus 1 includes an endoscope 2 inserted into a body cavity of a subject and adapted to output a signal of an image picked up of an object such as living tissue 101 in the body cavity, a light source device 3 adapted to give off illuminating light to illuminate the living tissue 101, a processor 4 adapted to apply various processes to an output signal from the endoscope 2, a display device 5 adapted to display images according to a video signal from the processor 4, and an external storage device 6 adapted to store an output signal according to processing results of the processor 4.

The endoscope 2 includes an insertion portion 21a sized and shaped so as to be able to be inserted into the body cavity of the subject, a distal end portion 21b installed on a distal end side of the insertion portion 21a, and an operation portion 21c installed on a proximal end side of the insertion portion 21a. Also, a light guide 7 is passed through the insertion portion 21a to transmit the illuminating light given off by the light source device 3 to the distal end portion 21b.

One end face (incident light end face) of the light guide 7 is detachably connected to the light source device 3. Another end face (emergent light end face) of the light guide 7 is placed near an illumination optical system (not shown) installed in the distal end portion 21b of the endoscope 2. With this configuration, the illuminating light given off by the light source device 3 is emitted to the living tissue 101 through the light guide 7 connected to the light source device 3 and then through the illumination optical system (not shown) installed in the distal end portion 21b.

An objective optical system 22 and a CCD 23 are installed in the distal end portion 21b of the endoscope 2, where the objective optical system 22 is adapted to form an optical image of an object while the CCD 23 is adapted to acquire an image by picking up the optical image formed by the objective optical system 22. Also, an imaging mode selector switch 24 is installed on an operation portion 21c of the endoscope 2, where the imaging mode selector switch 24 is used to give a command to switch imaging mode between normal-light imaging mode and narrow-band light imaging mode.

The light source device 3 includes a white light source 31 made up of a xenon lamp or the like, a rotating filter wheel 32 adapted to convert white light given off by the white light source 31 into frame-sequential illuminating light, a motor 33 adapted to rotationally drive the rotating filter wheel 32, a motor 34 adapted to move the rotating filter wheel 32 and the motor 33 in a direction perpendicular to an emission light path of the white light source 31, a filter wheel driving unit 35 adapted to drive the motors 33 and 34 under the control of the processor 4, and a condenser optical system 36 adapted to collect the illuminating light passing through the rotating filter wheel 32 and supply the collected light to the incident end face of the light guide 7.

Figure 2:
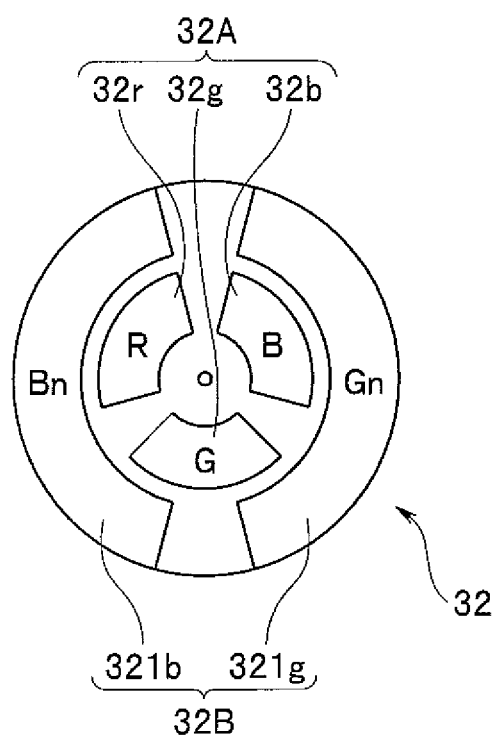
FIG. 2 is a diagram showing an exemplary configuration of a rotating filter wheel included in a light source device of FIG. 1.

As shown in FIG. 2, the rotating filter wheel 32 has a shape of a disk whose rotating shaft is located at a center and includes a first filter group 32A made up of a plurality of filters installed along a circumferential direction on an inner circumferential side and a second filter group 32B made up of a plurality of filters installed along a circumferential direction on an outer circumferential side. The rotating filter wheel 32 rotates when a driving force of the motor 33 is transmitted to the rotating shaft. Except for a part in which the filters of the first filter group 32A and second filter group 32B are placed, the rotating filter wheel 32 is made of a light-shielding material.

The first filter group 32A includes an R filter 32r, G filter 32g, and B filter 32b installed along the circumferential direction on the inner circumferential side of the rotating filter wheel 32, where the R filter transmits light in a red wavelength range, the G filter 32g transmits light in a green wavelength range, and the B filter 32b transmits light in a blue wavelength range.

Figure 3:
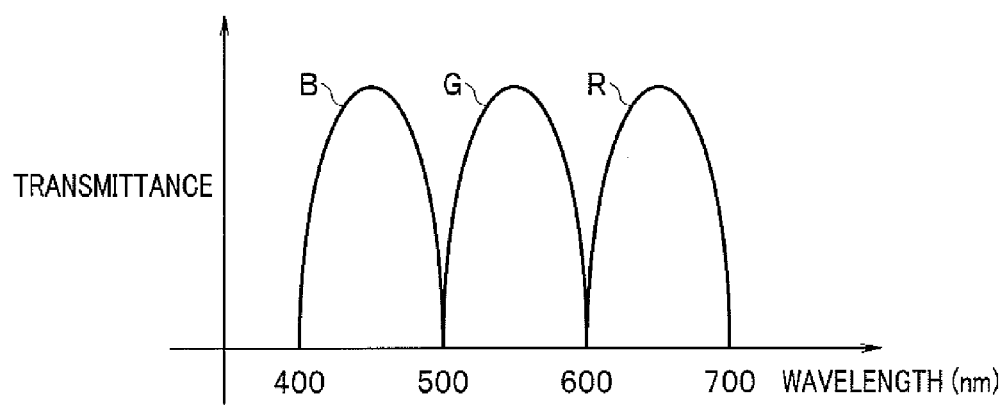
FIG. 3 is a diagram showing an example of transmission characteristics of each filter in a first filter group shown in FIG. 2.

The R filter 32r is configured to transmit light (R light) mainly in a range of 600 nm to 700 nm, for example, as shown in FIG. 3. The G filter 32g is configured to transmit light (G light) mainly in a range of 500 nm to 600 nm, for example, as shown in FIG. 3. The B filter 32b is configured to transmit light (B light) mainly in a range of 400 nm to 500 nm, for example, as shown in FIG. 3.

That is, the white light given off by the white light source 31 is changed into broad-band light for the normal-light imaging mode after passing through the first filter group 32A.

The second filter group 32B includes a Bn filter 321b and Gn filter 321g installed along the circumferential direction on the outer circumferential side of the rotating filter wheel 32, where the Bn filter 321b transmits blue and narrow-band light and the Gn filter 321g transmits green and narrow-band light.

Figure 4:
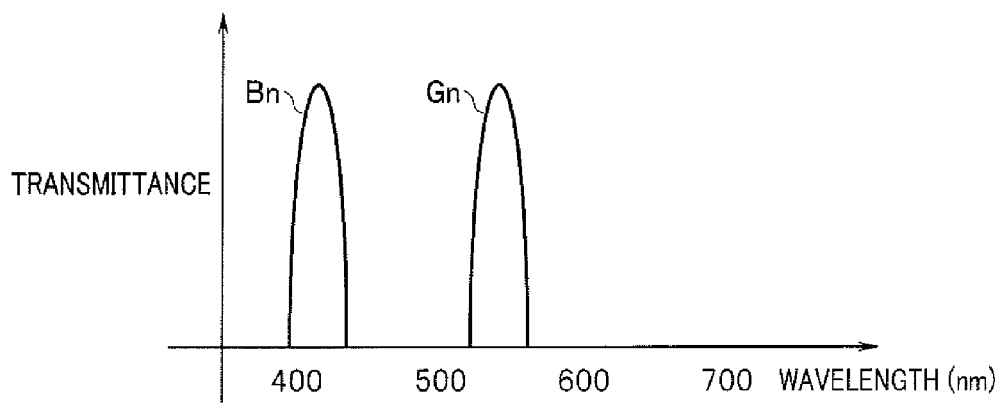
FIG. 4 is a diagram showing an example of transmission characteristics of each filter in a second filter group shown in FIG. 2.

The Bn filter 321b has a center wavelength set at around 415 nm and transmits light (Bn light) in a narrower band than B light, for example, as shown in FIG. 4.

The Gn filter 321g has a center wavelength set at around 540 nm and transmits light (Gn light) in a narrower band than G light, for example, as shown in FIG. 4.

That is, the white light given off by the white light source 31 is discretized by the second filter group 32B into multiple bands of narrow-band light for the narrow-band imaging mode.

The processor 4 is configured to serve functions of an image processing apparatus. Specifically, the processor 4 includes an image processing unit 41 and a control unit 42. The image processing unit 41 in turn includes an image data generating unit 41a, a computing unit 41b, and a video signal generating unit 41c.

Under the control of the control unit 42, the image data generating unit 41a of the image processing unit 41 applies noise reduction, A/D conversion, and other processes to an output signal of the endoscope 2 and thereby generates image data corresponding to images obtained by the CCD 23.

The computing unit 41b of the image processing unit 41 performs predetermined processing using the image data generated by the image data generating unit 41a and thereby extracts a candidate region estimated to contain a mucosal microstructure (histologic structure) of a predetermined shape from the image data. Details of the above-described predetermined processing will be described in detail later.

The video signal generating unit 41c of the image processing unit 41 applies gamma conversion, A/D conversion, and other processes to the image data generated by the image data generating unit 41a and thereby generates and outputs a video signal.

If it is detected that a command to switch to the normal-light imaging mode has been issued via the imaging mode selector switch 24, the control unit 42 performs control over the filter wheel driving unit 35 to cause the broad-band light for the normal-light imaging mode to be emitted from the light source device 3. Then, under the control of the control unit 42, the filter wheel driving unit 35 operates the motor 34 so as to insert the first filter group 32A in the emission light path of the white light source 31 and retract the second filter group 32B from the emission light path of the white light source 31.

On the other hand, if it is detected that a command to switch to the narrow-band imaging mode has been issued via the imaging mode selector switch 24, the control unit 42 performs control over the filter wheel driving unit 35 to cause the multiple bands of narrow-band light for the narrow-band imaging mode to be emitted from the light source device 3. Then, under the control of the control unit 42, the filter wheel driving unit 35 operates the motor 34 so as to insert the second filter group 32B in the emission light path of the white light source 31 and retract the first filter group 32A from the emission light path of the white light source 31.

That is, with the configuration of the endoscope apparatus 1 described above, when the normal-light imaging mode is selected, an image (normal-light image) having substantially the same coloration as when an object is viewed with the naked eye can be displayed on the display device 5 and stored in the external storage device 6. Also, with the configuration of the endoscope apparatus 1 described above, when the narrow-band imaging mode is selected, an image (narrow-band image) with blood vessels in the living tissue 101 highlighted can be displayed on the display device 5 and stored in the external storage device 6.

Now, operation of the endoscope apparatus 1 will be described.

First, after powering on various parts of the endoscope apparatus 1, a surgeon selects the normal-light imaging mode on the imaging mode selector switch 24. Then, by watching images displayed on the display device 5 when the normal-light imaging mode is selected, i.e., images having substantially the same coloration as when the object is viewed with the naked eye, the surgeon inserts the endoscope 2 into a body cavity and brings the distal end portion 21b close to a site where the living tissue 101 to be observed exists.

When the surgeon selects the normal-light imaging mode on the imaging mode selector switch 24, lights of different colors, i.e., R light, G light, and B light, are emitted in sequence from the light source device 3 to the living tissue 101, and images of the different colors are acquired through the endoscope 2.

Figure 5:
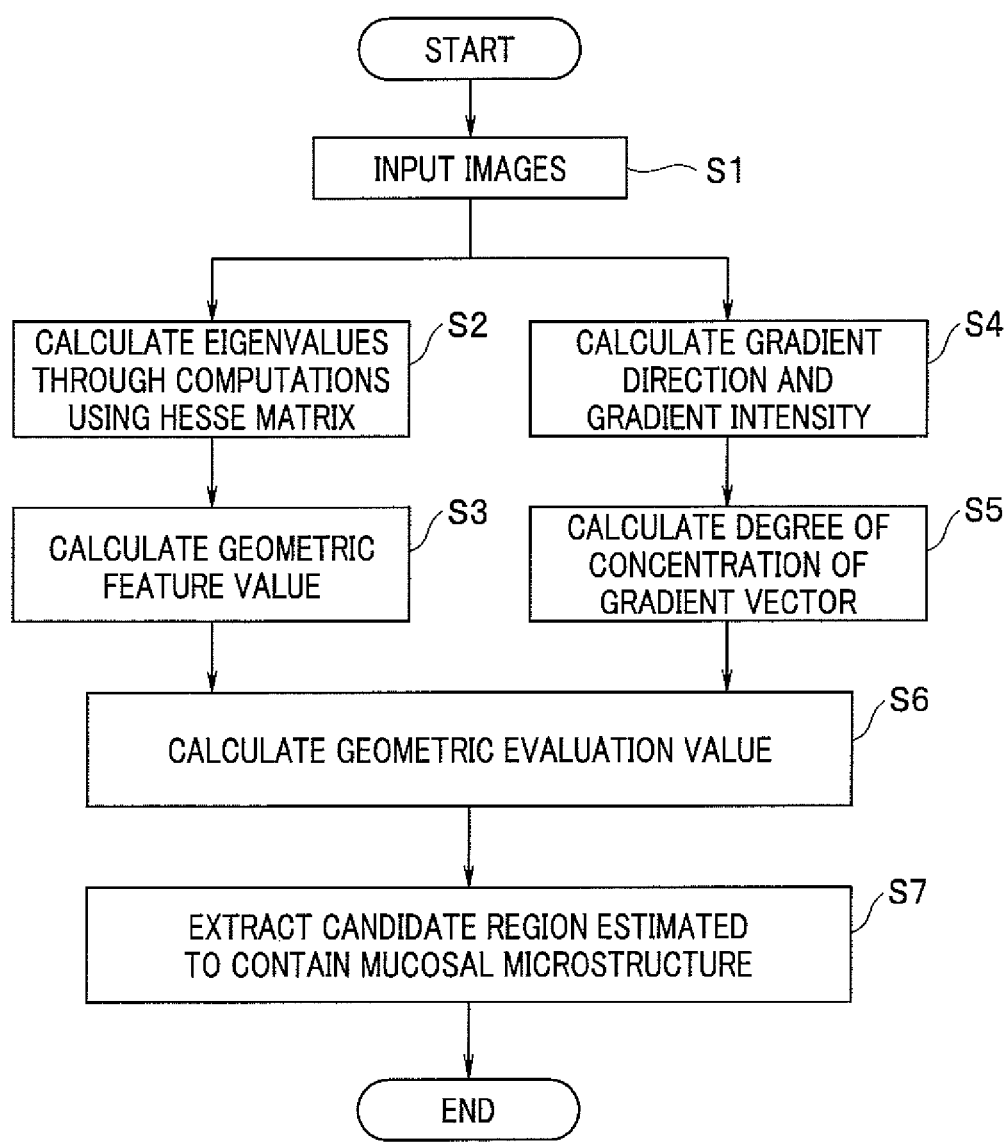
FIG. 5 is a flowchart showing an example of processing performed in the embodiment of the present invention.
Figure 6:
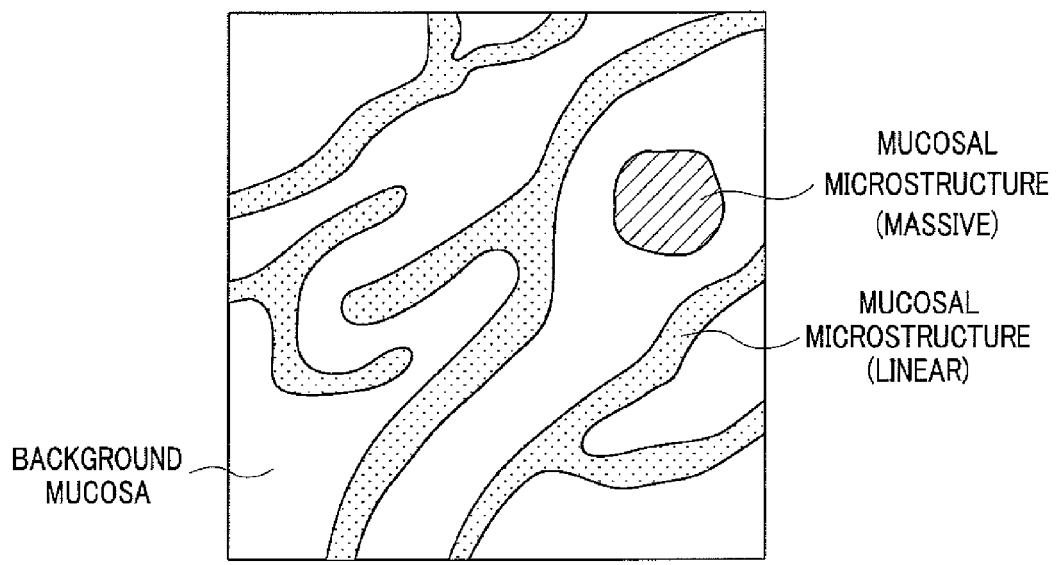
FIG. 6 is a schematic diagram showing an example of image data to be processed.

Upon receiving the image corresponding to the R light, the image corresponding to the G light, and the image corresponding to the B light, the image data generating unit 41a of the image processing unit 41 generates image data of color components corresponding to the respective images (Step S1 in FIG. 5). Incidentally, for simplicity of explanation, it is assumed in the following description that processing is performed on image data such as schematically shown in FIG. 6, in which a region corresponding to a linear mucosal microstructure (histologic structure) is indicated by a dot pattern, a massive mucosal structure (histologic structure) is indicated by a hatch pattern, a region corresponding to a background mucosa is indicated by white, and boundary lines among the three regions are indicated by fine solid lines.

The computing unit 41b performs computations using the Hesse matrix on the image data generated by the image data generating unit 41a and thereby calculates eigenvalues corresponding to the Hesse matrix on a pixel by pixel basis (Step S2 in FIG. 5).

Specifically, using the Hesse matrix H given by mathematical expression (1) below, the computing unit 41b performs computations disclosed in an article by Alejandro F. Frangi, et al. entitled "Multiscale Vessel Enhancement Filtering" (LNCS, vol. 1496, Springer Verlag, Berlin, Germany, pp. 130-137) on the image data generated by the image data generating unit 41a, and thereby calculates eigenvalues $\lambda 1$ and $\lambda 2$ (where $|\lambda 1| \geq |\lambda 2|$). Incidentally, the symbol L on the right-hand side of mathematical expression (1) below represents image intensity in a local location of the image, and corresponds to $L(x_0 + \delta x_0, s)$ in the article by Alejandro F. Frangi, et al. described above.

$$H = \begin{bmatrix} h_{11} & h_{12} \\ h_{21} & h_{22} \end{bmatrix} = \begin{bmatrix} \frac{\partial^2 L}{\partial x^2} & \frac{\partial^2 L}{\partial x \partial y} \\ \frac{\partial^2 L}{\partial x \partial y} & \frac{\partial^2 L}{\partial y^2} \end{bmatrix} \quad (1)$$

Subsequently, based on the eigenvalues $\lambda 1$ and $\lambda 2$ calculated in the process of Step S2 in FIG. 5, the computing unit 41b functioning as a first feature value calculation unit calculates, on a pixel by pixel basis, a geometric feature value representing an index which indicates approximately what shape a local region including a pixel of interest and each pixel in a neighborhood of the pixel of interest has (Step S3 in FIG. 5).

Specifically, the computing unit 41b performs computations using mathematical expression (2) below and thereby calculates a geometric feature value shape(s) of a pixel of interest s.

$$\text{shape}(s) = \begin{cases} 0 & \text{if } \lambda 1 \geq 0 \\ \exp\left(-\frac{R_\beta^2}{2\beta^2}\right) & \text{otherwise} \end{cases} \quad (2)$$

In mathematical expression (2) above, $R_\beta$ is a value obtained from $\lambda 2/\lambda 1$, where $\beta$ is a parameter set empirically (as a constant of, e.g., $\beta = 0.5$).

On the other hand, the computing unit 41b performs computations using output values obtained by the application of a primary differential filter such as a Sobel filter to the image data generated by the image data generating unit 41a and thereby calculates a gradient direction and a gradient intensity for each pixel (Step S4 in FIG. 5).

Subsequently, based on a gradient vector defined by the gradient direction and gradient intensity calculated in the process of Step S4 in FIG. 5, the computing unit 41b functioning as a second feature value calculation unit calculates a degree of concentration of the gradient vector for each pixel, where the degree of concentration of the gradient vector represents a state of distribution in the gradient direction in the local region.

Figure 7:
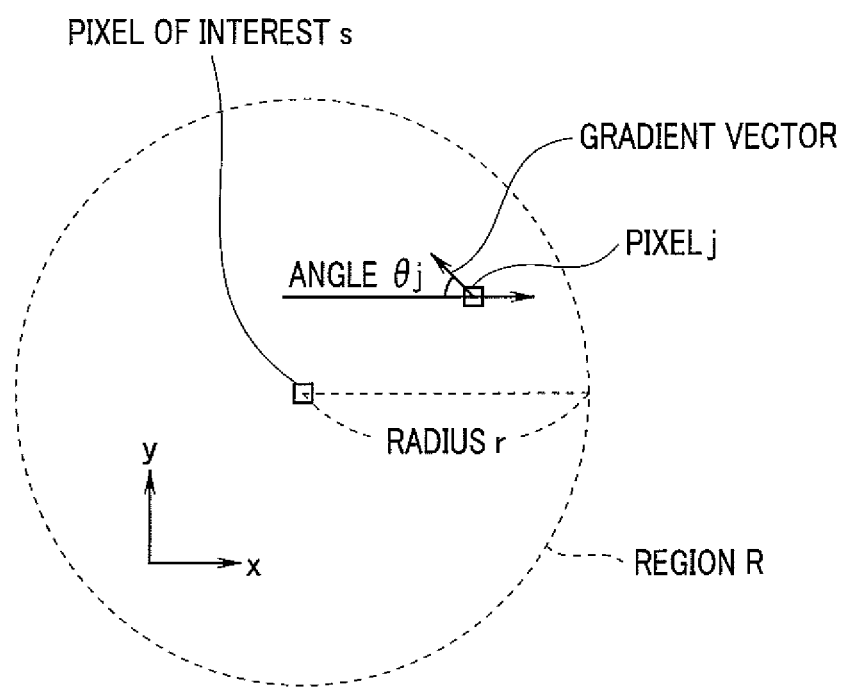
FIG. 7 is a diagram for illustrating elements used in calculating a degree of concentration of a gradient vector.

Specifically, for example, as shown in FIG. 7, the computing unit 41b sets a region R which is a circle of radius r with a center at the pixel of interest s as a search region and performs computations using mathematical expression (3) below and thereby calculates the degree of concentration of the gradient vector GC(s) in the pixel of interest s, where $\theta_j$ is an angle of the gradient vector defined by the gradient direction and gradient intensity of a pixel j in the region R with respect to a direction of an x axis (axial direction going from left to right in FIG. 7).

$$GC(s) = \frac{1}{M} \cdot \sum_R \cos \theta_j \quad (3)$$

In mathematical expression (3) above, M is the number of pixels whose gradient intensity is larger than 0 out of the pixels contained in the region R.

Incidentally, although the process of calculating the geometric feature value shape(s) (processes of Steps S2 and S3) and the process of calculating the degree of concentration of the gradient vector GC(s) (processes of Steps S4 and S5) are carried out concurrently in the present embodiment as shown in FIG. 5, this is not restrictive and one of the processes may be carried out before the other.

On the other hand, the computing unit 41b functioning as an evaluation value calculation unit performs computations using the geometric feature value shape(s) calculated through the processes of Steps S2 and S3 in FIG. 5 and the degree of concentration of the gradient vector GC(s) calculated through the processes of Steps S4 and S5 in FIG. 5, and thereby calculates, for each pixel, a geometric evaluation value which enables distinguishing between a linear mucosal structure and a massive mucosal structure (Step S6 in FIG. 5).

Specifically, the computing unit 41b performs computations using mathematical expression (4) below and thereby calculates the geometric evaluation value $v_0(S)$ of the pixel of interest s.

$$v_0(s) = \begin{cases} 0 & \text{if } \lambda 1 \geq 0 \\ \exp\left(-\frac{R_\beta^2}{2\beta^2}\right) \cdot \exp\left(-\frac{\{GC(s)\}^2}{2\gamma^2}\right) & \text{otherwise} \end{cases} \quad (4)$$

In mathematical expression (4) above, $\gamma$ is a parameter set empirically (as a constant of, e.g., $\gamma=0.5$).

Then, through computations using mathematical expression (4) above, the geometric evaluation value $v_0(S)$ is calculated so as to vary in value range among a pixel group containing a linear mucosal microstructure (histologic structure), a pixel group containing a massive mucosal structure (histologic structure), and a pixel group corresponding to a background mucosa.

By changing the arithmetic expression of the geometric evaluation value $v_0(S)$ depending on whether or not $\lambda 1 \geq 0$, mathematical expression (4) above is configured to allow detection of a relatively bright region in the image, i.e., a region containing a locally elevated (linear and/or massive) mucosal microstructure. However, this is not restrictive, and if the arithmetic expression of the geometric evaluation value $v_0(S)$ is changed depending on whether or not $\lambda 1 \geq 0$, mathematical expression (4) above will allow detection of a relatively dark region in the image, i.e., a region containing a locally recessed mucosal microstructure.

Incidentally, if one attempts to detect a mucosal microstructure in the image data generated by the image data generating unit 41a, by solely using the geometric feature value shape(s) obtained through the processes of Steps S2 and S3 in FIG. 5, although it is possible to approximately detect which shape a local region containing the pixel of interest s has, a linear shape or massive shape, one will get a detection result which could confuse a step edge attributable to a height difference (e.g., an edge of a blood vessel) on a surface of the living tissue with, for example, a ridge line of a mucosal microstructure.

On the other hand, if one attempts to detect a mucosal microstructure in the image data generated by the image data generating unit 41a, by solely using the degree of concentration of the gradient vector GC(s) obtained through the processes of Steps S4 and S5 in FIG. 5, although it is possible to detect, without depending on image contrast, whether or not a local region containing the pixel of interest s has an elevated shape (or recessed shape), it is not possible to obtain a detection result which will enable distinguishing which shape the local region has, a linear shape or massive shape.

In contrast, as shown by mathematical expression (4) above, the present embodiment calculates the geometric evaluation value $v_0(S)$ by combining two values—the geometric feature value shape(s) and the degree of concentration of the gradient vector GC(s). Thus, the present embodiment can detect, without depending on image contrast, which shape a local region containing the pixel of interest s has, a linear shape or massive shape while reducing the possibility of misdetecting the step edge described above as a ridge line of a mucosal microstructure.

On the other hand, using the geometric evaluation value $v_0(S)$ calculated for each pixel, the computing unit 41b functioning as a region extraction unit separately extracts a candidate region estimated to contain a linear mucosal microstructure and a candidate region estimated to contain a massive mucosal microstructure (Step S7 in FIG. 5).

Then, by performing the series of processes described above, it is possible to extract regions estimated to contain a pit pattern such as a linear structure or massive structure of a mucosal microstructure and regions estimated to contain a linear structure of blood vessels or the like, in a distinguishable manner, from an image such as shown in FIG. 6.

Incidentally, the present embodiment may process not only an image containing both linear and massive mucosal structures, but also an image containing one of linear and massive mucosal structures.

As described above, the present embodiment has a configuration and operation whereby a region estimated to contain a linear mucosal microstructure and a region estimated to contain a massive mucosal structure are separately extracted using the geometric evaluation value $v_0(S)$ which does not depend on image contrast. Thus, the present embodiment can stably detect structures of predetermined shapes even when the contrast of an image picked up of living tissue varies (fluctuates) greatly.

It should be noted that the present invention is not limited to the embodiment described above, and needless to say that various alterations and applications are possible without departing from the spirit of the invention.

What is claimed is:

1. An image processing apparatus comprising:
a first feature value calculation unit adapted to calculate a first feature value for each pixel in an image picked up of living mucosal structure based on eigenvalues obtained through computations using a Hesse matrix, where the first feature value represents a value of an index which indicates what shape a local region including a pixel of interest and each pixel in a neighborhood of the pixel of interest has;
a second feature value calculation unit adapted to calculate a degree of concentration of a gradient vector as a second feature value based on the gradient vector defined by a gradient direction and a gradient intensity calculated for each pixel in the image, where the degree of concentration of the gradient vector represents a state of distribution in the local region;
an evaluation value calculation unit adapted to calculate a geometric evaluation value for each pixel in the image, where a value which enables distinguishing between a linear mucosal structure and a massive mucosal structure contained in the image and which does not depend on contrast of the image is calculated as the geometric evaluation value based on calculation results of the first feature value and the second feature value; and
a region extraction unit adapted to separately extract a candidate region estimated to contain the linear mucosal structure and a candidate region estimated to contain the massive mucosal structure based on a calculation result of the geometric evaluation value.

2. A method of controlling an image processing apparatus for extracting a predetermined shape with respect to a medical image, the method performing:
a first feature value calculation step of calculating, by a first feature value calculation unit, a first feature value for each pixel in an image picked up of living mucosal structure based on eigenvalues obtained through computations using a Hesse matrix, where the first feature value represents a value of an index which indicates what shape a local region including a pixel of interest and each pixel in a neighborhood of the pixel of interest has;
a second feature value calculation step of calculating, by a second feature value calculation unit, a degree of concentration of a gradient vector as a second feature value based on the gradient vector defined by a gradient direction and a gradient intensity calculated for each pixel in the image, where the degree of concentration of the gradient vector represents a state of distribution in the local region;

an evaluation value calculation step of calculating, by an evaluation value calculation unit, a geometric evaluation value for each pixel in the image, where a value which enables distinguishing between a linear mucosal structure and a massive mucosal structure contained in the image and which does not depend on contrast of the image is calculated as the geometric evaluation value based on calculation results of the first feature value and the second feature value; and a region extraction step of separately extracting, by a region extraction unit, a candidate region estimated to contain the linear mucosal structure and a candidate region estimated to contain the massive mucosal structure based on a calculation result of the geometric evaluation value.

\* \* \* \* \*